United States Patent
Yao et al.

(10) Patent No.: US 10,813,756 B2
(45) Date of Patent: Oct. 27, 2020

(54) DELIVERY DEVICE

(71) Applicant: LIFETECH SCIENTIFIC (SHENZHEN) CO., LTD, Shenzhen (CN)

(72) Inventors: Bin Yao, Shenzhen (CN); Xiangdong Liu, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 204 days.

(21) Appl. No.: 16/311,282

(22) PCT Filed: May 10, 2017

(86) PCT No.: PCT/CN2017/083723
§ 371 (c)(1),
(2) Date: Dec. 19, 2018

(87) PCT Pub. No.: WO2018/000948
PCT Pub. Date: Jan. 4, 2018

(65) Prior Publication Data
US 2019/0183643 A1  Jun. 20, 2019

(30) Foreign Application Priority Data
Jul. 1, 2016  (CN) .......................... 2016 1 0518125

(51) Int. Cl.
*A61F 2/95* (2013.01)
*A61F 2/24* (2006.01)

(52) U.S. Cl.
CPC .............. *A61F 2/2436* (2013.01); *A61F 2/95* (2013.01)

(58) Field of Classification Search
CPC .. A61F 2/95; A61F 2/962; A61F 2/966; A61F 2002/9505; A61F 2/2436
See application file for complete search history.

(56) References Cited

U.S. PATENT DOCUMENTS

| 2010/0268315 A1* | 10/2010 | Glynn ........................ A61F 2/95 623/1.11 |
| 2013/0144380 A1 | 6/2013 | Quadri et al. |
| 2013/0231735 A1* | 9/2013 | Deem ....................... A61F 2/243 623/2.11 |

(Continued)

FOREIGN PATENT DOCUMENTS

| CN | 102869321 A | 1/2013 |
| CN | 102905647 A | 1/2013 |

(Continued)

OTHER PUBLICATIONS

International Search Report dated Jul. 19, 2017 in corresponding International Application No. PCT/CN2017/083723; 9 pages.

*Primary Examiner* — Wade Miles
(74) *Attorney, Agent, or Firm* — Maier & Maier, PLLC

(57) ABSTRACT

A delivery device used for delivering a heart valve, a blood vessel stent, and the like. The device includes a first stopper and a connecting unit. The connecting unit is provided opposite to the first stopper and can move relative to the first stopper. The connecting unit includes an axial connecting portion and at least two axial shafts. The axial shaft is connected to the connecting portion and faces the first stopper. The connecting unit is used to form, together with the first stopper, an enclosed and locked space.

17 Claims, 10 Drawing Sheets

(56) References Cited

U.S. PATENT DOCUMENTS

| | | | | |
|---|---|---|---|---|
| 2013/0274870 A1* | 10/2013 | Lombardi | ............ | A61F 2/2436 |
| | | | | 623/2.11 |
| 2014/0018911 A1* | 1/2014 | Zhou | ...................... | A61F 2/966 |
| | | | | 623/2.11 |
| 2014/0067037 A1* | 3/2014 | Fargahi | .................... | A61F 2/95 |
| | | | | 623/1.12 |
| 2014/0067050 A1* | 3/2014 | Costello | ................. | A61F 2/966 |
| | | | | 623/2.11 |
| 2014/0081375 A1* | 3/2014 | Bardill | ..................... | A61F 2/95 |
| | | | | 623/1.12 |
| 2014/0277345 A1* | 9/2014 | Havel | .................... | A61F 2/966 |
| | | | | 623/1.11 |
| 2014/0309680 A1 | 10/2014 | Fargahi | | |
| 2015/0142101 A1* | 5/2015 | Coleman | ......... | A61B 17/12031 |
| | | | | 623/2.11 |
| 2015/0265442 A1* | 9/2015 | Styrc | ........................ | A61F 2/95 |
| | | | | 623/1.11 |
| 2016/0015543 A1* | 1/2016 | Perouse | ................. | A61F 2/962 |
| | | | | 623/1.12 |
| 2016/0128819 A1* | 5/2016 | Giordano | .............. | A61B 50/30 |
| | | | | 206/570 |
| 2017/0216068 A1* | 8/2017 | Dwyer | ................... | A61F 2/966 |

FOREIGN PATENT DOCUMENTS

| | | |
|---|---|---|
| CN | 202892148 U | 4/2013 |
| CN | 103857361 A | 6/2014 |

\* cited by examiner

DELIVERY DEVICE

FIELD

Embodiments of the present application relate to the field of medical devices, and more particularly relate to a delivery device for delivering an implanted medical device.

BACKGROUND

To accurately place a medical device (such as a blood vessel stent, a heart valve, a heart defect occluder, a blood vessel occluder and a blood vessel filter) and a drug to a predetermined part of a human heart or arteriovenous vessel with an intervention technology, a delivery device must be used, which generally includes a delivery sheath, a guidewire and a pusher. An implantation process of a device includes: building a delivery channel by using the guidewire; guiding the distal end of the delivery sheath by the guidewire to the predetermined part; removing the guidewire; putting the medical device into the delivery sheath, and pushing it to the distal end of the delivery sheath by using the pusher; and releasing the medical device. If the medical device is found to be implanted at a non-ideal position in the releasing process, it is required to be withdrawn into the delivery sheath for relocating and then is released again. Finally, the medical device is separated from the pusher, and the delivery device is withdrawn out of the body so as to complete the implantation process.

A self-expansion type medical device may easily pop out due to its outward expansion force when released from the distal end of the delivery sheath, which may apply a relatively high instantaneous impulsive force to a tissue of the implantation part, possibly resulting in tissue injury.

SUMMARY

In view of this, an exemplary embodiment of the present application provides a delivery device, which may prevent a tissue from being injured so as to reduce risk and injury to a human body.

The delivery device includes a first stopper and a connecting unit. The connecting unit is disposed opposite to the first stopper and may move relative to the first stopper. The connecting unit includes a radial connecting portion and at least two axial shafts which are connected with the radial connecting portion and face to the first stopper. The connecting unit cooperates with the first stopper to form a closed lock space.

In one exemplary embodiment, the delivery device further includes a second stopper disposed opposite to the first stopper. When the connecting unit cooperates with the first stopper to form the lock space, the second stopper is located in the lock space.

In one exemplary embodiment, the second stopper and the first stopper form a stop unit of the delivery device. The delivery device further includes a push rod and a sheath core which is arranged on the push rod in a penetrating manner and may move relative to the push rod. The connecting unit is arranged on the push rod, the stop unit is arranged on the sheath core, and the connecting unit is closer to the proximal end of the delivery device than the stop unit. Or, the connecting unit is arranged on the sheath core, the stop unit is arranged on the push rod, and the stop unit is closer to the proximal end of the delivery device than the connecting unit.

In one exemplary embodiment, a first blocking member is arranged on the push rod, a second blocking member matched with the first blocking member is arranged on the sheath core, and the first blocking member is closer to the distal end of the delivery device than the second blocking member. When the first blocking member is in contact with the second blocking member, the push rod is static relative to the sheath core.

In one exemplary embodiment, the second stopper includes multiple stop blocks. One stop block corresponds to at least one axial shaft.

In one exemplary embodiment, the multiple stop blocks are separated from one another.

In one exemplary embodiment, one stop block corresponds to one of the axial shafts. Each stop block includes two opposite and parallel clamping units, and the circumferential thickness of the axial shaft corresponding to the stop block is less than a circumferential distance between the two clamping units of the stop block corresponding to the same axial shaft.

In one exemplary embodiment, the end, which is close to the center axis of the sheath core, of each stop block is in contact with the end, which is close to the center axis of the sheath core, of the adjacent stop block to form a whole (or be integrally formed), and the other ends, which are away from the center axis of the sheath core, of the multiple stop blocks are separated from one another.

In one exemplary embodiment, one stop block corresponds to two axial shafts. The connecting unit includes at least two connecting pieces, each of which includes two opposite and parallel connecting subpieces. Each connecting subpiece includes one axial shaft. The outer diameter of each stop block is greater than the inner diameters of the two axial shafts corresponding to the same stop block, and less than the outer diameters of the two axial shafts corresponding to the same stop block. The circumferential thickness of each stop block is less than a distance between the two axial shafts corresponding to the same stop block.

In one exemplary embodiment, the second stopper includes multiple stop blocks, each of which corresponds to one axial shaft. Each stop block includes two opposite and parallel clamping units. The circumferential thickness of the proximal end of each axial shaft is greater than that of the rest part of the same axial shaft. The circumferential thickness of the proximal end of the same axial shaft is greater than a circumferential distance between the two clamping units of the stop block corresponding to the same axial shaft. The circumferential thickness of the rest part of the same axial shaft is less than the circumferential distance between the two clamping units of the stop block corresponding to the same axial shaft.

In one exemplary embodiment, the connecting unit includes at least two connecting pieces, each of which includes two opposite connecting subpieces. Each connecting subpiece includes one axial shaft. A blocking strip is erected between the two axial shafts of each connecting piece.

In one exemplary embodiment, the second stopper includes multiple stop blocks, each of which corresponds to one axial shaft. An axial through-hole which penetrates through the inner side surface and the outer side surface of one axial shaft and does not penetrate through the end face of the free end of the axial shaft is formed in the axial shaft. The free end of one stop block may be movably accommodated in the axial through-hole.

In one exemplary embodiment, the connecting unit includes at least two connecting pieces, each of which includes two opposite connecting subpieces. Each connecting subpiece includes one axial shaft. A blocking strip is erected between the two axial shafts of each connecting piece.

In one exemplary embodiment, the second stopper includes multiple stop blocks, each of which corresponds to one axial shaft. An axial through-hole which penetrates through the inner side surface and the outer side surface of one axial shaft and does not penetrate through the end face of the free end of the axial shaft is formed in the axial shaft. The free end of one stop block may be movably accommodated in the axial through-hole.

In one exemplary embodiment, the radial connecting portion includes at least two radial shafts. One end of each axial shaft is connected with one radial shaft to substantially form an L shape.

In one exemplary embodiment, at least one connecting ring is arranged on the radial connecting portion, and the other end of the connecting ring is a free end.

In one exemplary embodiment, the first stopper includes at least two stop cavities, each of which may accommodate the free end of at least one axial shaft.

In one exemplary embodiment, each stop cavity is a through-hole penetrating through the proximal-end surface and the distal-end surface of the first stopper or a groove which is sunken from part of the side surface of the first stopper towards the center of the first stopper and penetrates through the proximal-end surface and the distal-end surface of the first stopper.

In one exemplary embodiment, the inner side surface of the radial connecting portion is connected with the inner side surfaces of at least two axial shafts to form a hemispherical surface.

In one exemplary embodiment, the outer side surface of the radial connecting portion is connected with the outer side surfaces of at least two axial shafts to form a hemispherical surface.

Compared with the prior art, embodiments of the delivery device of the present application include the axial shafts, so that movement of a joint of a medical device and the delivery device is restricted by the axial shafts in a process of releasing the medical device. The medical device may, in one embodiment, be completely separated from the delivery device only when completely separated from the axial shafts, thereby buffering the outward expansion force of the medical device and reducing risk and a likelihood of injury to the human body.

DETAILED DESCRIPTION

To make the above-mentioned objectives, features and advantages of the present application more understandable, specific implementation modes of the present application are described below in details in combination with accompanying drawings. The following descriptions elaborate many specific details to fully understand the present application, but the present application may be implemented in many other modes different from the description herein. Persons skilled in the art can make similar improvements without departing from the scope of the present application, so that the present application is not limited by the specific implementation modes disclosed below.

It should be noted that when one element is called "fixed" to another element, it may be directly on another element, or a centered element may exist. When one element is deemed as being "connected" to another element, it may be directly connected to another element or a centered element may exist at the same time. In the interventional field, the end closer to an operator is generally called the proximal end, and the end farther from the operator is called the distal end. It should be further noted that when "circumferential direction" is described, it is the "circumferential direction", and when "axial direction" is described, it is the "axial direction" or the "lengthwise direction".

It should be noted that the exemplary embodiments below are described by taking a delivery device for a replacement artificial heart valve or an occluder as an example. The concept of the present application also may be applied to delivery devices of other implanted devices, such as, but not limited to, a blood vessel stent and a heart defect occluder.

Unless otherwise defined, technical and scientific terms used herein have the same meanings as general understandings of technicians in the technical field. The terms used in the description of the present application are only to describe specific exemplary embodiments, but not intended to limit the scope of the present application. The term "and/or" used herein includes any and all combinations of one or multiple relevant listed items.

Figure 1:
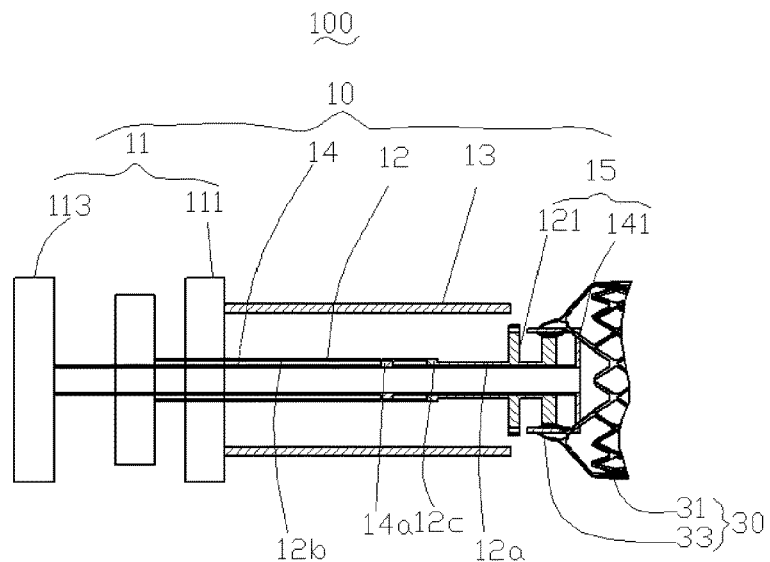
FIG. 1 is an exemplary structure schematic diagram of a delivery system provided by a first embodiment of the present application.

Referring to exemplary FIG. 1, a medical device delivery system 100 provided by a first embodiment of the present application includes a delivery device 10 and a medical device 30 detachably connected with the delivery device 10. The medical device 30 may be an artificial mitral valve or other artificial heart valves such as an artificial tricuspid valve, an artificial aortic valve or an artificial pulmonary valve. The medical device 30 also may be other implanted devices, such as, but not limited to, a blood vessel stent or a heart defect occluder.

The delivery device 10 includes a handle 11, a hollow push rod 12, a sheath 13, a sheath core 14, and a lock member 15. The sheath core 14 penetrates through the push rod 12, with one end connected with the handle 11 and the other end connected with the lock member 15.

The handle 11 includes a sheath actuator 111 and a sheath core actuator 113. Under the action of an external force, the sheath actuator 111 and the sheath core actuator 113 are respectively used for actuating the sheath 13 and the sheath core 14 to move relative to the push rod 12.

The push rod 12 is accommodated in the sheath 13 and surrounds the sheath core 14. The sheath 13 surrounds the push rod 12, with the proximal end connected with the sheath actuator 111 and the distal end extending towards the distal end of the delivery device 10. A first blocking member 12c is arranged on the push rod 12. In the present embodiment, the push rod 12 has a hollow first section 12a and a hollow second section 12b which are communicated with each other. The inner diameter of the first section 12a is less than that of the second section 12b. The annular first blocking member 12c, which is an annular blocking step, is formed at a joint of the first section 12a and the second section 12b of the push rod 12.

The proximal end of the sheath core 14 is connected with the sheath core actuator 113, and the distal end of the sheath core 14 extends towards the distal end of the delivery device 10. The sheath core 14 may move relative to the push rod 12 under the actuation of the sheath core actuator 113. The sheath core 14 is provided with a second blocking member 14a cooperatively used with the first blocking member 12c. In the exemplary embodiment, the outer wall of the sheath core 14 is provided with the second blocking member 14a which is an annular blocking convex block and is far from the distal end of the delivery device 10 relative to the first blocking member 12c. When the second blocking member 14a is in contact with the first blocking member 12c, the sheath core 14 may not move in the axial direction relative to the push rod 12, namely the second blocking member 14a and the first blocking member 12c can cooperate with each other to control a distance between a sheath core 14 and the lock member 15. In other embodiments, when the first blocking member 12c is an annular or non-annular blocking convex block arranged on the inner wall of the push rod 12, an annular or non-annular step used as the second blocking member 14a is formed on the sheath core 14, which also may implement blocking. The first and second blocking members may formed to be non-annular, for example, each of which may include multiple mutually separated blockers located on the same circumference. Or, the first and second blocking members may be of other arbitrary shapes as long as they may cooperate with each other to limit the relative motion of the sheath core 14 and the push rod 12 in the axial direction. It can be understood that the first and the second in the first blocking member and the second blocking member are only used to describe the present application more clearly, and may not limit the patent scope of the present application. That is to say, the second blocking member 14a of the sheath core 14 also may be called the first blocking member 14a, and accordingly, the first blocking member 12c on the push rod 12 also may be called the second blocking member 12c.

Figure 2:
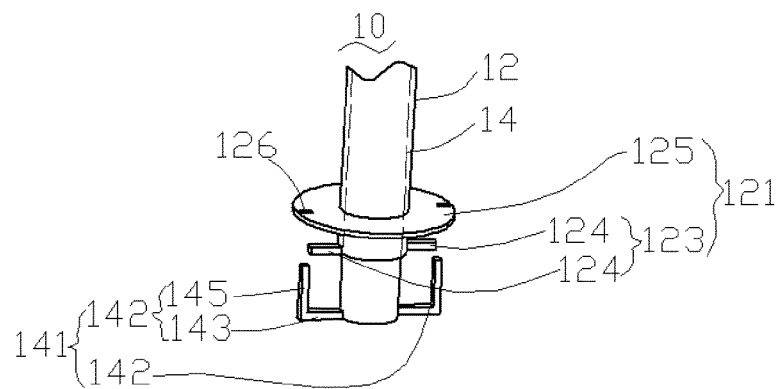
FIG. 2 is an exemplary schematic diagram of a delivery device of the delivery system in FIG. 1.

The lock member 15 includes a stop unit 121 arranged at the distal end of the push rod 12 and the connecting unit 141 arranged on the sheath core 14. The stop unit 121 is used to cooperate with the connecting unit 141 to control the interconnection and disconnection between the medical device 30 and the delivery device 10. Referring to FIG. 2 as well, the stop unit 121 includes a first stopper 125 and a second stopper 123 which are both fixed at the distal end of the push rod 12, wherein the second stopper 123 is closer to the distal end of the push rod 12 than the first stopper 125.

The second stopper 123 includes at least two mutually separated stop blocks 124. One end of each stop block 124 is connected to the push rod 12, and the other end of the stop block 124 is radially extending from the surface of the push rod 12 towards a direction away from the push rod 12. In the present embodiment, to show a position relation and a connection relation among the stop blocks 124, the first stopper 125 and the connecting unit 141 more clearly, only two strip-type stop blocks 124 are provided, which are located in the extending direction of the same diameter of the push rod 12.

It can be understood that in other embodiments, multiple stop blocks 124 of other shapes except the strip type may be provided, but channels allowing the connecting unit 141 to move relative to the first stopper 125 are reserved between the stop blocks 124. For example, all the stop blocks 124 may be separated from one another, and a gap between two adjacent stop blocks 124 forms each channel Or, the end, which is close to the center axis of the sheath core 14, of each stop block 124 is in contact and connected with the end, which is close to the center axis of the sheath core 14, of the adjacent stop block 124, so as to form a whole, but the other ends, which are far away from the center axis of the sheath core 14, of the multiple stop blocks 124 are separated from one another. For example, all the stop blocks 124 can cooperate to form a gear-like shape, and gaps between gear teeth form the channels. It can be further understood that in other embodiments, the second stopper 123 may be omitted as required.

The first stopper 125 surrounds the push rod 12 and is provided with at least two stop cavities 126. In the present embodiment, each stop cavity 126 is a through-hole penetrating through the proximal-end surface and the distal-end surface of the first stopper 125. In other embodiments, each stop cavity 126 also may be sunken from part of the side surface of the first stopper 125 towards the center of the first stopper 125 and penetrate through the proximal-end surface and the distal-end surface of the first stopper 125. Or, each stop cavity 126 is a groove formed in the distal-end surface of the first stopper 125. The number of the stop cavities 126 is the same as that of the stop blocks 124. In the present embodiment, the outer diameter of the first stopper 125 is greater than that of the second stopper 123. A projection of the second stopper 123 on the first stopper 125 is closer to the push rod 12 than each stop cavity 126, and a projection of each stop block 124 on the first stopper 125 and each corresponding stop cavity 126 are located on the same diameter of the first stopper 125.

The connecting unit 141 is used to cooperate with the first stopper 125 to form a closed lock space 17 (referring to FIG. 4 and FIG. 2) so as to prevent the medical device 30 from being detached from the delivery device 10 before releasing, and the connecting unit 141 includes at least two connecting pieces 142. In the present embodiment, the number of the connecting pieces 142 is the same as that of the stop blocks 124 and that of the stop cavities 126, and each connecting piece 142 corresponds to a stop block 124. Each connecting piece 142 is approximately of an L shape, and includes a radial shaft 143 and an axial shaft 145. One end of each radial shaft 143 is connected with the sheath core 14, and the other end of the radial shaft 143 is far away from the sheath core 14 and is connected with the axial shaft 145 of the same connecting piece 142. The multiple radial shafts 143 are combined to form a radial connecting portion of the connecting unit 141. The lock space 17 is formed under the cooperation of the axial shafts 145 and the first stopper 125 in order to prevent the medical device 30 from being detached from the delivery device 10 before releasing, and it is encircled by a surface formed by connecting the outer side surfaces of the multiple radial shafts 143, a surface formed by connecting the outer side surfaces of the multiple axial shafts 145 and the first stopper 125. One end of each axial shaft 145 is connected with the end portion, which is far away from the sheath core 14, of the radial shaft 143 of the same connecting piece 142, and the other end of each axial shaft 145 is a free end and extends towards the proximal end of the sheath core 14. The free end of each axial shaft 145 may be movably accommodated in each corresponding stop cavity 126. In other embodiments, smooth chamfers may be arranged at intersections of the radial shafts 143 and the axial shafts 145. In other embodiments, two adjacent radial shafts in the multiple radial shafts 143 also may be in contact and connected with each other to be integrally formed, such as a disk-like structure which is the radial connecting portion of the connecting unit 141 at this moment.

Figure 3:
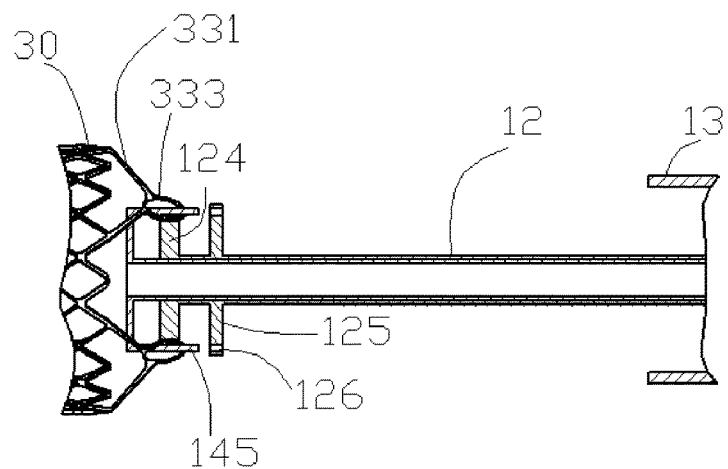
FIG. 3 is an exemplary schematic diagram showing that a medical device in FIG. 1 is connected to the delivery device in FIG. 2.
Figure 4:
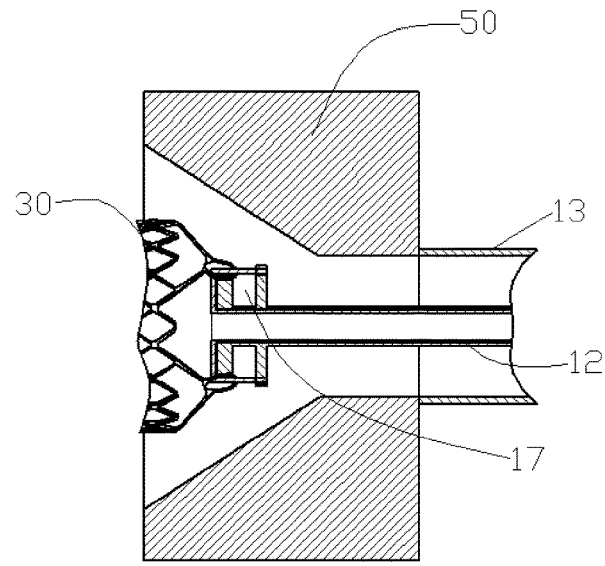
FIG. 4 is an exemplary schematic diagram of an initial state of compressing the medical device connected to the delivery device into a sheath by using a loader.

Referring to FIG. 2, and FIGS. 3 to 4 together, when the free end of each axial shaft 145 is accommodated in each stop cavity 126, the free end of each stop block 124 is in contact with the axial shaft 145, and the medical device 30 may be hung on the axial shaft 145 and located in the space encircled by the axial shaft 145, the stop block 124 and the first stopper 125, and may not be detached from the connecting unit 141.

Referring to FIG. 1 again, the medical device 30 includes a hollow main body portion 31 and an artificial valve (not shown in the figure) arranged in the main body portion 31. The main body portion 31 is of a mesh structure formed by weaving metal wires or cutting and setting a tube stock and is used for bearing the artificial valve. In the present embodiment, the main body portion 31 is of a mesh structure formed by cutting and setting a nickel-titanium metal tube stock. In other embodiments, a stent main body may be formed by weaving and setting nickel-titanium wires, and also may be formed by weaving macromolecular wires such as polycarbonate wires, polypropylene wires and polyamide wires which are made of a macromolecular material or cutting and setting a macromolecular tube stock made of the macromolecular material.

Referring to FIG. 1 and FIG. 3 together, the medical device 30 further includes multiple connecting portions 33 connected with the main body portion 31. The number of the connecting portions 33 is less than or equal to that of the connecting pieces 142 so as to enable each connecting portion 33 to be connected to one connecting piece 142. In the present embodiment, the number of the connecting portions 33 is equal to that of the connecting pieces 142.

Each connecting portion 33 includes two connecting strips 331 connected with the main body portion 31 and a connecting ring 333 connected with the end portions, which are far away from the main body portion 31, of the two connecting strips 331.

Figure 5:
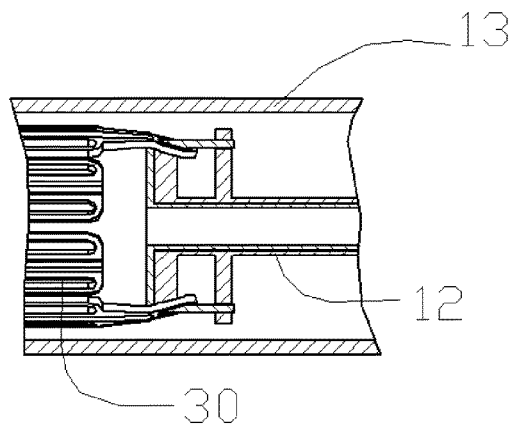
FIG. 5 is an exemplary schematic diagram of the compressed medical device in the sheath.

When the medical device 30 is required to be preserved in an anti-calcification solution, the delivery device 10 and the medical device 30 are required to be packaged separately. Before the surgical operation, a loader 50 is used to load the medical device 30 into the delivery device 10 by referring to the following steps. First, the sheath actuator 111 is used to actuate the sheath 13 to move relative to the push rod 12, towards the proximal end until the lock member 15 is completely extended out of the sheath 13. Second, the sheath core actuator 113 is used to actuate the sheath core 14 to move relative to the push rod 12 towards the distal end, and the moving sheath core 14 actuates the axial shafts 145 of the lock member 15 to move towards the distal end until the free ends of the axial shafts 145 are completely withdrawn from the stop cavities 126 and the stop blocks 124 are in contact with the axial shafts 145 and located at the middle positions of the axial shafts 145. Third, referring to FIG. 3, the multiple connecting rings 333 of the medical device 30 are hung onto the corresponding axial shafts 145 one by one. Then, the sheath core actuator 113 is used to actuate the sheath core 14 to move relative to the push rod 12 towards the proximal end, and the moving sheath core 14 actuates the connecting unit 141 to move towards the proximal end until the free ends of the axial shafts 145 enter the corresponding stop cavities 126 of the first stopper 125 so as to implement the connection between the medical device 30 and the delivery device 10. Finally, referring to FIG. 4, a loader 50 is arranged on the medical device 30 in a sleeving manner, and the sheath actuator 111 is used to actuate the sheath 13 to move relative to the push rod 12 towards the distal end and actuate the loader 50 to move along with the sheath 13 towards the distal end until the medical device 30 may be completely put into the sheath 13 in a compressed state, as shown in FIG. 5. After a delivery channel is built, the distal end of the delivery device 10 with the medical device 30 is delivered to a position near to a lesion.

It can be understood that in other exemplary embodiments, a gap may be also reserved between the free end of each stop block 124 and each axial shaft 145 as long as each connecting ring 333 may not pass through this gap to enter the space encircled by the axial shaft 145 hanging the same connecting ring 333, the stop block 124 corresponding to the same axial shaft 145 and the radial connecting portion.

Figure 6:
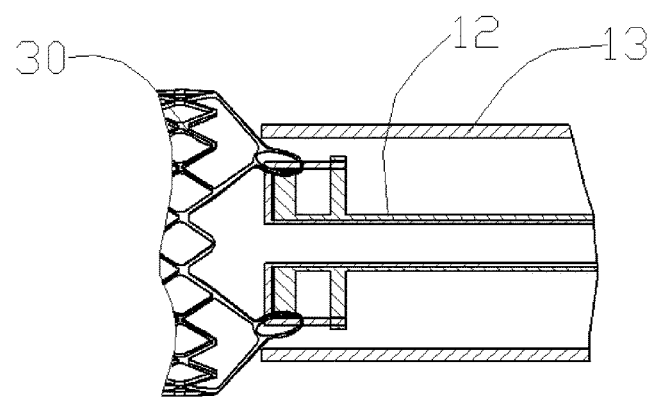
FIG. 6 is an exemplary schematic diagram showing that the medical device is released from the sheath and a lock member of the delivery device is still in the sheath.

Referring to FIG. 6, when the medical device 30 has arrived at the position near to the lesion, the sheath actuator 111 is used to actuate the sheath 13 to slowly move relative to the push rod 12 towards the proximal end. The medical device 30 is gradually changed from the compressed state to an expanded state due to its self-expandability when the radial restriction from the sheath 13 to the medical device 30 disappears gradually in a process that the sheath 13 moves towards the proximal end. After the medical device 30 is completely extended out of the sheath 13, an operator observes whether the medical device 30 achieves the therapeutic effect or not. If the medical device 30 is located at a non-ideal or undesired position, the sheath actuator 111 may be used to actuate the sheath 13 to move relative to the push rod 12 towards the distal end, and the medical device 30 is compressed into the sheath 13 again. To adjust the position of the medical device 30, the above steps can be repeated, if necessary, until the medical device 30 achieves an ideal or desired therapeutic effect.

Figure 7:
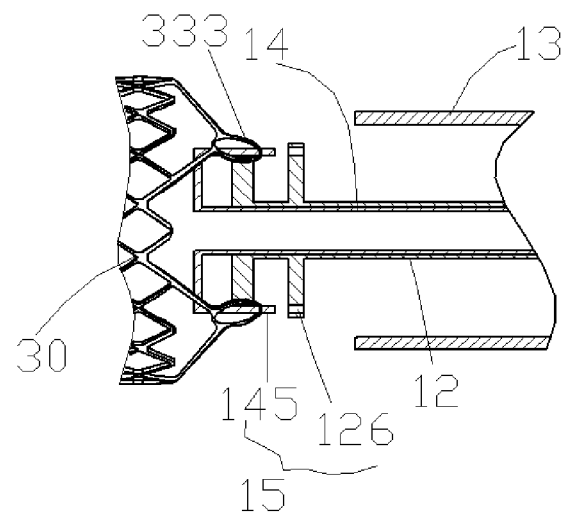
FIG. 7 is an exemplary schematic diagram showing that the lock member of the delivery device is exposed from the sheath and axial shafts of the lock member are separated from a first stopper.
Figure 8:
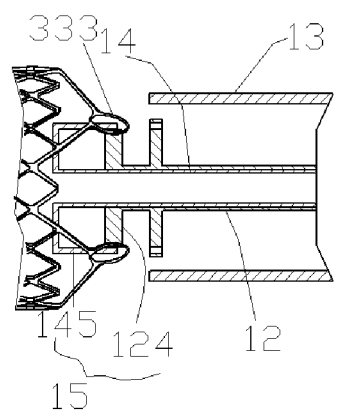
FIG. 8 is an exemplary schematic diagram showing that the medical device is about to be separated from the lock member.
Figure 9:
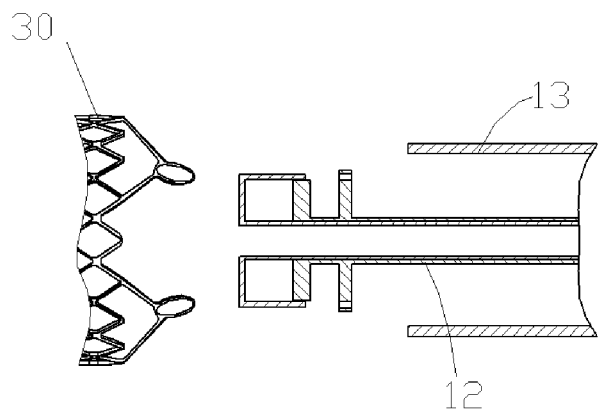
FIG. 9 is an exemplary schematic diagram showing that the medical device is completely separated from the lock member.

After the medical device 30 achieves an expected or desired therapeutic effect on the lesion, the sheath actuator 111 may be used again to actuate the sheath 13 to move relative to the push rod 12 towards the proximal end until the lock member 15 is completely exposed from the sheath 13. Then, referring to exemplary FIGS. 7 to 9 together, the sheath core actuator 113 actuates the sheath core 14 to move relative to the push rod 12 towards the distal end, and the moving sheath core 14 actuates the axial shafts 145 to move relative to the stop blocks 124 towards the distal end. That is, the connecting rings 333 can move relative to the axial shafts 145 towards the proximal end under the pushing force of the corresponding stop blocks 124. When the free ends of the axial shafts 145 move to be flush with the proximal ends of the outer sides (which are the farthest to the sheath core 14) of the stop blocks 124, namely when the first blocking member 12c is in contact with the second blocking member 14a, so as to prevent the axial shafts 145 from continuously moving relative to the stop blocks 124 towards the distal end. The connecting rings 333 may be separated from the free ends of the axial shafts 145 under the pushing force of the stop blocks 124. At that point, the medical device 30 is completely detached from the delivery device 10, thereby completing the releasing of the medical device 30. Because of the fact that the free ends of the axial shafts 145 can move to be flush with the proximal ends of the outer sides of the stop blocks 124, the connecting rings 333 may be no longer hooked by the axial shafts 145 after the medical device 30 is released, thereby guaranteeing the safety and the smoothness of the operation.

It should be noted that in the present embodiment, referring to exemplary FIG. 1, FIG. 2, and FIG. 4 together, when the axial shafts 145 cooperate with the first stopper 125 to form the lock space 17, the distance between the proximal end of the first blocking member 12c and the distal end of the second blocking member 14a along the axial direction of the delivery device 10 is equal to the distance between the free end of each axial shaft 145 and the proximal end of the outer side of each stop block 124 along the axial direction of the delivery device 10, so that when the first blocking member 12c is in contact with the second blocking member 14a to prevent the axial shafts 145 from continuously moving relative to the stop blocks 124 towards the distal end, the free ends of the axial shafts 145 may be flush with the proximal ends of the outer sides of the stop blocks 124.

It can be understood that in other embodiments, when the axial shafts 145 cooperate with the first stopper 125 to form the lock space 17, the distance between the proximal end of the first blocking member 12c and the distal end of the second blocking member 14a along the axial direction of the delivery device 10 is equal to the distance between the free end of each axial shaft 145 and the distal end of the outer side of each stop block 124 along the axial direction of the delivery device 10, so that when the first blocking member 12c is in contact with the second blocking member 14a to prevent the axial shafts 145 from continuously moving relative to the stop blocks 124 towards the distal end, the free ends of the axial shafts 145 may be flush with the distal ends of the outer sides of the stop blocks 124. When the axial shafts 145 cooperate with the first stopper 125 to form the lock space 17, the distance between the proximal end of the first blocking member 12c and the distal end of the second blocking member 14a along the axial direction of the delivery device 10 is greater than the distance between the free end of each axial shaft 145 and the proximal end of the outer side of each stop block 124 along the axial direction of the delivery device 10 and is less than the distance between the free end of each axial shaft 145 and the distal end of the outer side of each stop block 124 along the axial direction of the delivery device 10, so that when the first blocking member 12c is in contact with the second blocking member 14a to prevent the axial shafts 145 from continuously moving relative to the stop blocks 124 towards the distal end, the free ends of the axial shafts 145 may be located between the proximal ends and the distal ends of the outer sides of the stop blocks 124. In either of the above-mentioned cases, the free ends of the axial shafts 145 may no longer hook the medical device 30 after the medical device 30 is released.

It can be understood that in other exemplary embodiments, when the free ends of the stop blocks 124 move to be flush with the distal ends of the outer sides of the axial shafts 145, or when the free ends of the stop blocks 124 move to be located between the distal ends of the outer sides of the axial shafts 145 and the proximal ends of the outer sides of the axial shafts 145, the first blocking member 12c can be in contact with the second blocking member 14a to prevent the axial shafts 145 from moving axially relative to the stop blocks 124 and also to prevent the connecting rings 333 from being hooked by the axial shafts 145 again, thereby guaranteeing the safety and the smoothness of the operation. It is important to note that if the relative movement between each axial shaft 145 and each stop block 124 is controlled only through the handle 11 in a process of implanting the medical device, it is very hard for the handle 11 to accurately control the relative axial movement between the axial shaft 145 and the stop block 124 as the handle located outside the body is relatively far from the axial shaft 145 and the stop block 124 which are both located inside the body, and a slippery hand of an operator or overexertion during operation of the handle 11 may cause relatively high difficulty in accurately controlling the relative axial movement between the axial shaft 145 and the stop block 124, which increases the possibility of separation of the axial shaft 145 and the stop block 124. In the present embodiment, the first blocking member 12c and the second blocking member 14a, which are separated from the handle 11, are respectively arranged on the push rod 12 and the sheath core 14, so that when the first blocking member 12c is in contact with the second blocking member 14a, the relative axial movement between each axial shaft 145 and each stop block 124 is restricted. That is, the arrangement of the first blocking member 12c and the second blocking member 14a may further restrain the relative axial movement between each axial shaft 145 and each stop block 124, which improves the accuracy of controlling the relative axial movement between each axial shaft 145 and each stop block 124 and reducing the separation possibility of the axial shaft 145 and the stop block 124.

In other embodiments, the connecting unit 141 may be arranged on the push rod 12, and accordingly, a stop unit 121 is arranged on the sheath core 14 and is coaxial with the connecting unit 141. At the moment, the lock member 15 includes the connecting unit 141, the second stopper 123, and the first stopper 125 in sequence from the proximal end to the distal end, and the free ends of the axial shafts 145 of the connecting unit 141 face to the first stopper 125. That is, the free ends of the axial shafts 145 are closer to the first stopper 125 than the radial connecting portion of the connecting unit 141. When the connecting unit 141 moves axially relative to the stop unit 121, the free ends of the axial shafts 145 may cooperate with the first stopper 125 to connect the device 30 with the delivery device 10, or the free ends of the axial shafts 145 may be separated from the first stopper 125 to detach the device 30 from the delivery device 10. It should be noted that in the present embodiment of this paragraph, when the axial shafts 145 cooperate with the first stopper 125 to form the lock space 17, the distance between the proximal end of the first blocking member 12c and the distal end of the second blocking member 14a along the axial direction of the delivery device 10 is equal to the distance between the free end of each axial shaft 145 and the distal end of the outer side of each stop block 124 along the axial direction of the delivery device 10, so that when the first blocking member 12c is in contact with the second blocking member 14a to prevent the axial shafts 145 from continuously moving relative to the stop blocks 124 towards the proximal end, the free ends of the axial shafts 145 may be flush with the distal ends of the outer sides of the stop blocks 124. It can be understood that in other embodiments, when the axial shafts 145 cooperate with the first stopper 125 to form the lock space 17, the distance between the proximal end of the first blocking member 12c and the distal end of the second blocking member 14a along the axial direction of the delivery device 10 is equal to the distance between the free end of each axial shaft 145 and the proximal end of the outer side of each stop block 124 along the axial direction of the delivery device 10, so that when the first blocking member 12c is in contact with the second blocking member 14a to prevent the axial shafts 145 from continuously moving relative to the stop blocks 124 towards the proximal end, the free ends of the axial shafts 145 may be flush with the proximal ends of the outer sides of the stop blocks 124. When the axial shafts 145 cooperate with the first stopper 125 to form the lock space 17, the distance between the proximal end of the first blocking member 12c and the distal end of the second blocking member 14a along the axial direction of the delivery device 10 is greater than the distance between the free end of each axial shaft 145 and the distal end of the outer side of each stop block 124 along the axial direction of the delivery device 10 and is less than the distance between the free end of each axial shaft 145 and the proximal end of the outer side of each stop block 124 along the axial direction of the delivery device 10, so that when the first blocking member 12c is in contact with the second blocking member 14a to prevent the axial shafts 145 from continuously moving relative to the stop blocks 124 towards the proximal end, the free ends of the axial shafts 145 may be located between the proximal ends and the distal ends of the outer sides of the stop blocks 124. In either of the above-mentioned cases, the free ends of the axial shafts 145 may no longer hook the medical device 30 after the medical device 30 is released.

It can be understood that in other embodiments, if no stop cavity 126 is formed in the first stopper 125, and when the free ends of the axial shafts 145 are in contact with the end face of the first stopper 125, the aim of preventing the medical device 30 from being separated from the delivery device 10 may be achieved as well.

Figure 10:
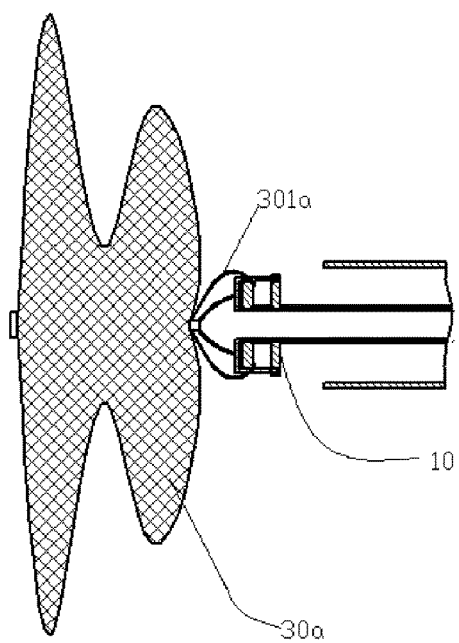
FIG. 10 is an exemplary schematic diagram of connection between the medical device which is an occluder and the delivery device.

Referring to FIG. 10, as an occluder, the medical device 30a may be connected with the delivery device 10 through connecting rings 301a arranged thereon to implement controllable release of the present application.

Figure 11:
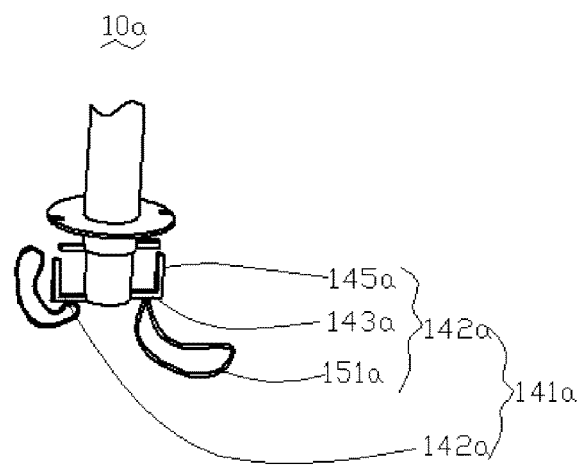
FIG. 11 is an exemplary schematic diagram of a delivery device of a delivery system provided by a second embodiment of the present application.

Referring to FIG. 11, a delivery device 10a provided by a second embodiment of the present application is substantially the same as the delivery device 10. A difference lies in that a connecting unit 141a of the delivery device 10a is different from the connecting unit 141. Specifically, each connecting piece 142a of the connecting unit 141a further includes a connecting ring 151a besides a radial shaft 143a and an axial shaft 145a which are connected with each other. One end of each connecting ring 151a is connected to the distal end face of each corresponding radial shaft 143, and the other end of each connecting ring 151a is a free end.

Figure 12:
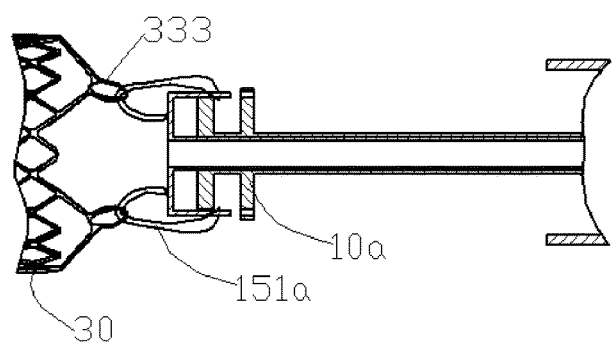
FIG. 12 is an exemplary schematic diagram showing that the medical device is hung on the delivery device in FIG. 11.

Referring to FIG. 12 together, putting the medical device 30 into the delivery device 10a through a loader (not shown in the figure) includes the following steps: the free end of each connecting ring 151a is threaded through one connecting ring 333 of the medical device 30, and the free end of each connecting ring 151a connected with the connecting ring 333 is hung onto each corresponding axial shaft 145a of the delivery device 10a. Other steps are basically the same as the implantation steps in the first embodiment, so that no more details will be described herein.

Figure 13:
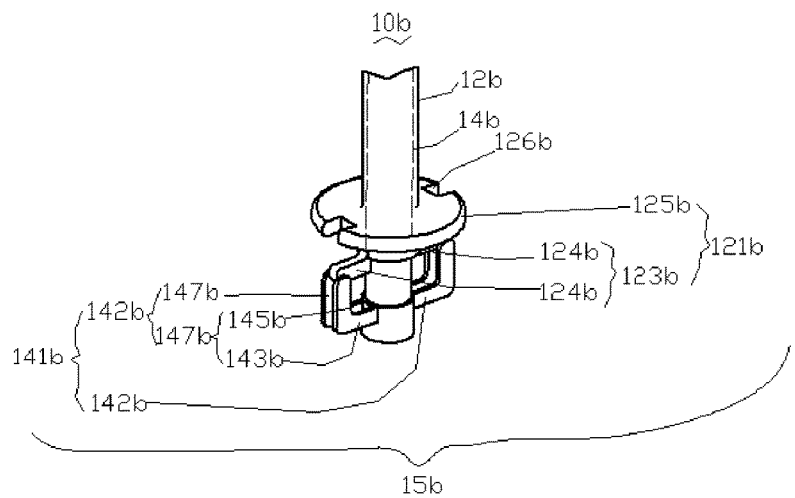
FIG. 13 is an exemplary structure schematic diagram of a delivery device provided by a third embodiment of the present application.
Figure 14:
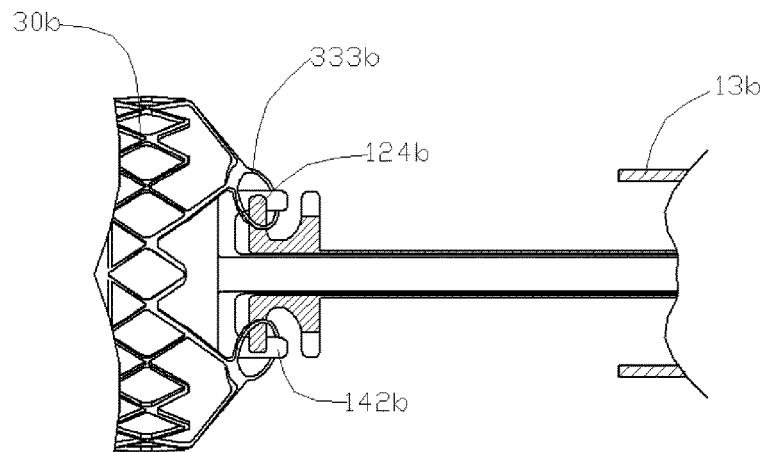
FIG. 14 is an exemplary schematic diagram showing that the medical device in FIG. 13 is hung on the delivery device.

Referring to FIG. 13 and FIG. 14, a delivery device 10b provided by a third embodiment of the present application is basically the same as the delivery device 10, and includes a hollow push rod 12b, a sheath 13b, a sheath core 14b and a lock member 15b. A difference lies in that the lock member 15b of the delivery device 10b is of a structure different from that of the lock member 15.

For example, each stop cavity 126b of a first stopper 125b of a stop unit 121b of the lock member 15b is sunken from part of the side surface of the first stopper 125b towards the center of the first stopper 125b and penetrates through the proximal-end surface and the distal-end surface of the first stopper 125b. Each connecting piece 142b of the connecting unit 141b of the lock member 15b includes two opposite and parallel connecting subpieces 147b.

Each connecting subpiece 147b includes a radial shaft 143b and an axial shaft 145b which are connected with each other. One end of the radial shaft 143b of each connecting subpiece 147b is connected with the sheath core 14b, and the other end of the radial shaft 143b is far away from the sheath core 14b and is connected with the axial shaft 145b of the same connecting subpiece 147b. One end of the axial shaft 145b of each connecting subpiece 147b is connected with the end portion, which is far away from the sheath core 14*b*, of the radial shaft 143*b* of the same connecting subpiece 147*b*, and the other end (namely the free end) of the axial shaft 145*b* extends towards the proximal end of the sheath core 14*b*.

The free ends of the two axial shafts 145*b* of each connecting piece 142*b* may both be movably accommodated in the corresponding stop cavities 126*b* so as to prevent the medical device 30*b* from being separated from the connecting unit 141*b* when the stop unit 121*b* cooperates with the connecting unit 141*b* to control the connection between the medical device 30*b* and the delivery device 10*b*.

In the present embodiment, one stop block 124*b* corresponds to the two axial shafts 145*b* of one connecting piece 142*b*. The outer diameter of each stop block 124*b* is greater than the inner diameters of the two axial shafts 145*b* corresponding to the same stop block 124*b* and less than the outer diameters of the two axial shafts 145*b* corresponding to the same stop block 124*b*. Furthermore, the circumferential thickness of each stop block 124*b* is slightly less than the circumferential distance between the two corresponding axial shafts 145*b*, so that the end portion, which is far away from the sheath core 14*b*, of each stop block 124*b* may move between the two axial shafts 145*b* of the corresponding connecting piece 142*b* instead of moving axially, and each stop block 124*b* may be accommodated between the two corresponding radial shafts 143*b*.

Figure 15:
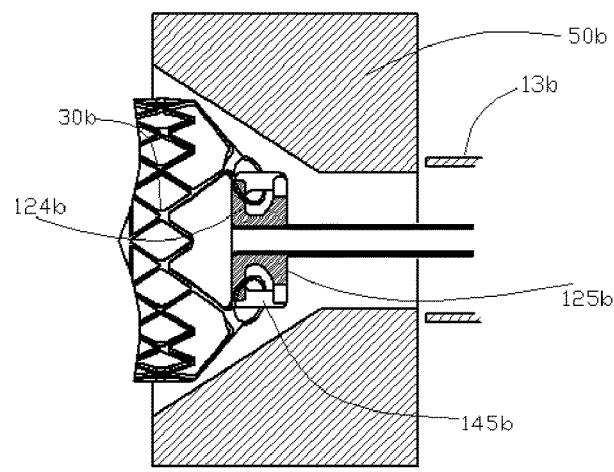
FIG. 15 is an exemplary schematic diagram of an initial state of compressing the medical device connected to the delivery device into a sheath by using a loader.
Figure 16:
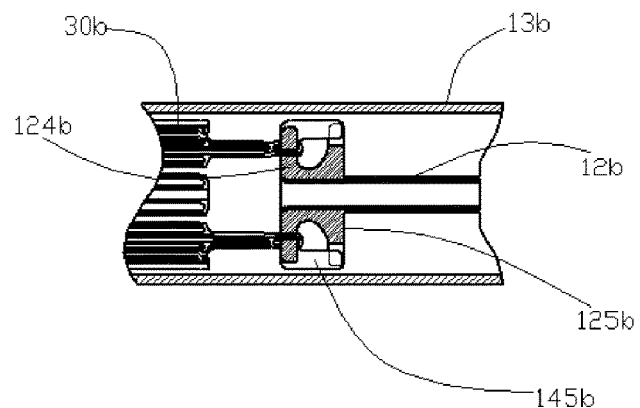
FIG. 16 is an exemplary schematic diagram of the compressed medical device in the sheath.

Putting the medical device 30*b* into the delivery device 10*b* includes the following steps: first, referring to FIG. 14, the multiple connecting rings 333*b* of the medical device 30*b* are hung onto the two axial shafts 145*b* of the corresponding connecting piece 142*b* one by one, and each connecting ring 333*b* is onto the corresponding stop block 124*b*; second, the sheath core 14*b* is actuated to move relative to the push rod 12*b* towards the proximal end, and the moving sheath core 14*b* actuates the connecting unit 121*b* to move towards the proximal end until the free ends of the axial shafts 145*b* enter the corresponding stop cavities 126*b* of the first stopper 125*b*, and each stop block 124*b* is accommodated between the two connecting subpieces 147*b* of the corresponding connecting piece 142*b*; and finally, referring FIG. 15 and FIG. 16, as in the first embodiment, a loader 50*b* is arranged on the medical device 30*b* in a sleeving manner, the sheath 13*b* is actuated to move relative to the push rod 12*b* towards the distal end, and the loader is actuated to move along with the sheath 13*b* towards the distal end until the medical device 30*b* may be completely put into the sheath 13*b* in a compressed state.

It can be understood that the push rod and the sheath core in the present embodiment also may be respectively provided with the first blocking member and the second blocking member as in the first embodiment, so as to prevent the free ends of the axial shafts 145*b* from hooking the medical device 30 after the medical device 30 is released.

Figure 17:
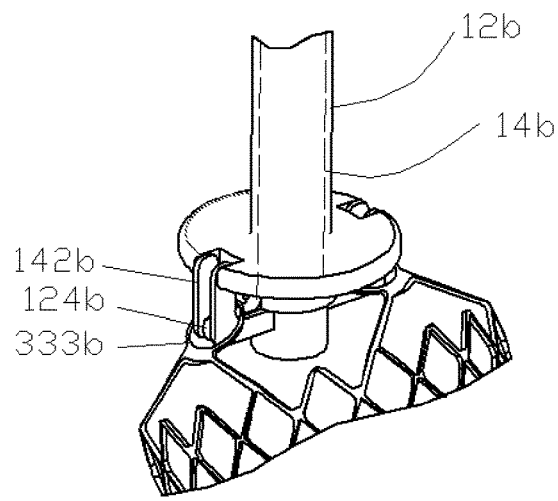
FIG. 17 is an exemplary schematic diagram showing that the medical device is released from the sheath and axial shafts of the delivery device are still in a first stopper.

After delivery channels are built in a human body, the distal end of the delivery device 10*b* with the medical device 30*b* is delivered to a lesion position. Referring to FIG. 16 and FIG. 17 again, when the medical device 30*b* has arrived at an appointed position, the sheath 13*b* is actuated to slowly move relative to the push rod 12*b* towards the proximal end. The medical device 30*b* is gradually changed from the compressed state to an expanded state due to its self-expandability when the radial restriction from the sheath 13*b* to the medical device 30*b* disappears gradually and the connecting rings 333*b* of the medical device 30*b* move outwards along the radial directions of the radial shafts 143*b* in a process that the sheath 13*b* moves towards the proximal end. After the whole medical device 30*b* completely extends out of the sheath 13*b*, an operator observes whether the medical device 30*b* full achieves its effect and meets a requirement or not. If the medical device 30*b* is located at a non-ideal position, the sheath 13*b* is actuated to move relative to the push rod 12*b* towards the distal end, and the medical device 30*b* is compressed into the sheath 13*b* again in this process. To adjust the position of the medical device 30*b*, the above steps can be repeated if necessary until the medical device 30*b* achieves an ideal therapeutic effect. After the medical device 30*b* achieves an expected therapeutic effect on the lesion, the sheath 13*b* is required to be actuated again to move relative to the push rod 12*b* towards the proximal end until the whole lock member 15 is completely exposed.

Figure 18:
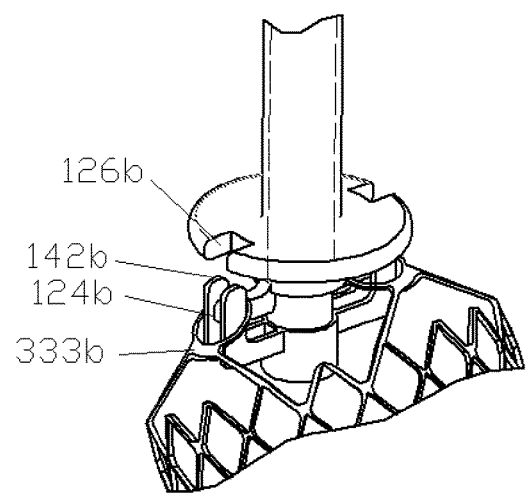
FIG. 18 is an exemplary schematic diagram showing that the axial shafts are separated from the first stopper.
Figure 19:
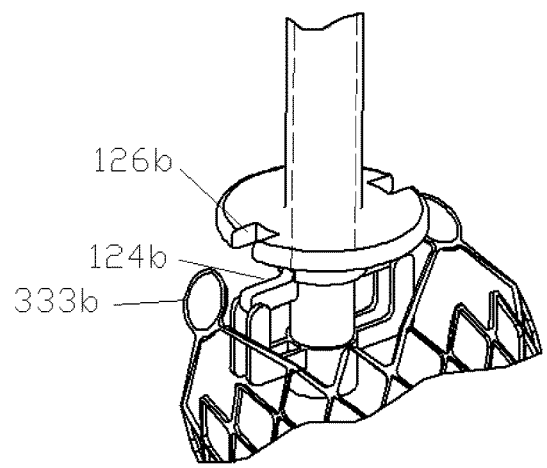
FIG. 19 is an exemplary three-dimensional schematic diagram showing that the medical device is completely separated from the lock member.
Figure 20:
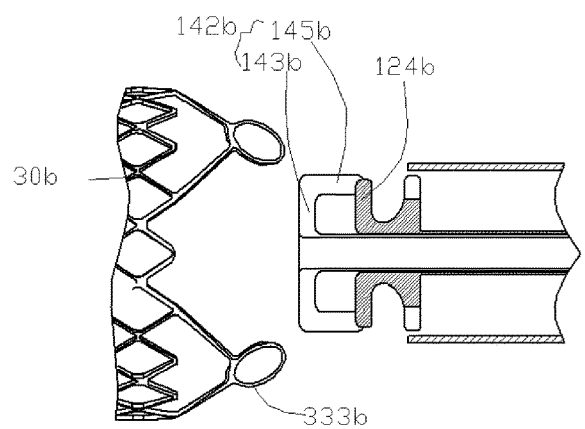
FIG. 20 is an exemplary schematic diagram from another angle after the medical device is completely separated from the lock member.

Then, referring to FIGS. 18 to 20 together, the sheath core 14*b* is actuated to move relative to the push rod 12*b* towards the distal end, and the moving sheath core 14*b* actuates the connecting pieces 142*b* to move relative to the stop blocks 124*b* towards the distal end (that is, the connecting rings 333*b* move relative to the connecting pieces 142*b* towards the proximal end under the pushing of the stop blocks 124*b*) until the free ends of the connecting pieces 142*b* are separated from the corresponding stop cavities 126*b* and the connecting rings 333*b* are completely separated from the axial shafts 145*b* of the connecting pieces 142*b*. At the moment, the medical device 30*b* is completely separated from the lock member 15*b* of the delivery device 10*b*, thereby completing the process of releasing the medical device 30*b*.

It can be known from the above structural description, loading process and implantation process, by cooperative use of the stop unit 121*b* and the connecting unit 141*b*, on one hand, the circumferential movement of each stop block 124*b* is restrained by each corresponding connecting piece 142*b*, which prevents a great distortion of each connecting ring, connected with each stop block 124*b*, of the medical device in the circumferential direction and reducing the possibility of movement of the medical device in the circumferential direction, and on the other hand, because of the fact that each stop block 124*b* may be accommodated between the two radial shafts 143*b* of each corresponding connecting piece 142*b*, each connecting ring, connected with each stop block 124*b*, of the medical device may move on the two radial shafts 143*b* of each corresponding connecting piece 142*b*, which buffers the outward expansion force of the medical device and lowering the injury to the human body. In addition, the circumferential thickness of each stop block 124*b* is slightly less than the distance between the two axial shafts 145*b* of each corresponding connecting piece 142*b*, so that a gap between the two axial shafts 145*b* of each corresponding connecting piece 142*b* may be filled with each stop block 124*b*, thereby preventing each connecting ring of the released medical device from being hooked by the free end of each axial shaft 145*b* again and improving the releasing efficiency of the medical device. Moreover, when the lock member 15*b* in the present embodiment is used to connect the connecting rings of the medical device, the connecting rings of the medical device may be hung onto the two radial shafts 143*b* of one connecting piece 142*b*, that is, the connecting rings of the medical device may be closer to the center axis of the sheath core 14*b*, so that the medical device accommodated by the delivery device 10*b* in the present embodiment has a relatively small compressed outer diameter.

It should be further noted that each stop block 124*b* may be accommodated between the two radial shafts 143*b* of each corresponding connecting piece 142b, so that compared with the design of the inner diameter size of each connecting ring of the medical device 30 of Embodiment I, it can not consider the influence caused by the size of the stop block 124b on the inner diameter size of each connecting ring of the medical device 30b when the design of the inner diameter size of each connecting ring of the medical device 30b Therefore, the inner diameter size of each connecting ring of the medical device 30b may be relatively reduced. It can be understood that in other embodiments, the inner side surfaces, which are close to an inner cavity encircled by a plurality of connecting pieces 142b, of the plurality of connecting pieces 142b may be connected to form a hemispherical surface such that the radial movement of the connecting rings of the medical device 30b may be changed into axial movement more smoothly. It can be further understood that in other embodiments, the outer side surfaces, which are far away from the inner cavity encircled by the plurality of connecting pieces 142b, of the plurality of connecting pieces 142b may be connected to form a hemispherical surface so as to facilitate machining and manufacturing.

Figure 21:
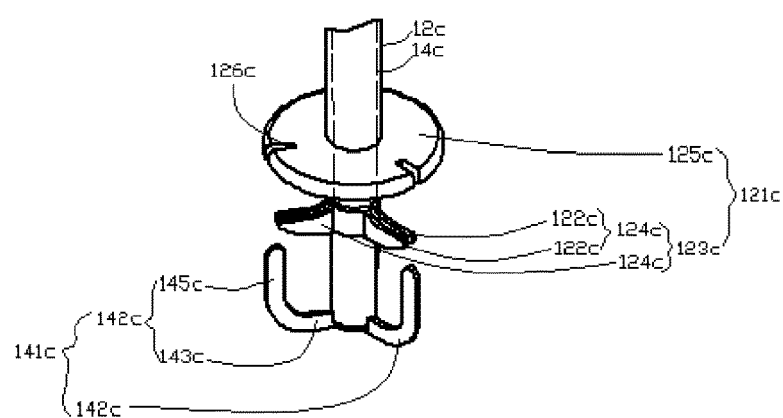
FIG. 21 is an exemplary structure schematic diagram of a delivery device provided by a fourth embodiment of the present application.
Figure 22:
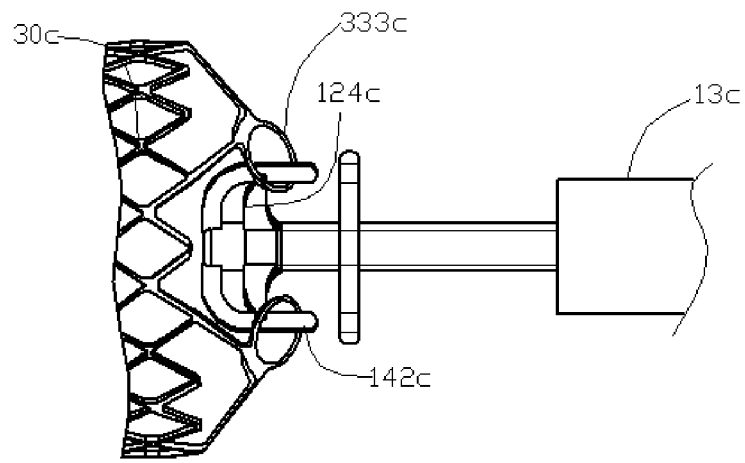
FIG. 22 is an exemplary schematic diagram showing that the medical device in FIG. 21 is hung on the delivery device.

Referring to FIGS. 21 and 22, a delivery device 10c of a fourth embodiment of the present application is basically the same as the delivery device 10, and includes a hollow push rod 12c, a sheath 13c, a sheath core 14c and a lock member 15c. A difference lies in that the lock member 15c of the delivery device 10c is different from the lock member 15.

In the embodiment, each stop cavity 126c of a first stopper 125c of the lock member 15c is a groove which is sunken from the side surface of part of the first stopper 125c towards the center of the first stopper 125c and penetrates through the proximal-end surface and the distal-end surface of the first stopper 125c, and there are three stop cavities 126c.

Each stop block 124c of a second stopper 123c of the lock member 15c includes two opposite and parallel clamping units 122c.

A connecting unit 141c of the lock member 15c includes three connecting pieces 142c, each of which includes a radial shaft 143c and an axial shaft 145c which are connected with each other. One end of the radial shaft 143c of each connecting piece 142c is connected with the sheath core 14c, and the other end of the radial shaft 143c is far away from the sheath core 14c and is connected with the axial shaft 145c of the same connecting piece 142c. One end of the axial shaft 145c of each connecting piece 142c is connected with the end portion, which is far away from the sheath core 14c, of the radial shaft 143c of the same connecting piece 142c, and the other end (namely the free end) of the axial shaft 145c extends towards the proximal end of the sheath core 14c. The free end of the axial shaft 145c of each connecting piece 142c may be movably accommodated in the corresponding stop cavity 126c so as to prevent the medical device 30c from being separated from the connecting unit 141c when the stop unit 121c cooperates with the connecting unit 141c to control the connection between the medical device 30c and the delivery device 10c.

For example, in the present embodiment, one axial shaft 145c corresponds to one stop block 124c. The outer diameter of each axial shaft 145c is less than or equal to that of each corresponding stop block 124c. The circumferential thickness of each axial shaft 145c is uniform, and is slightly less than the circumferential distance between the two parallel clamping units 122c of each corresponding stop block 124c, so that each connecting rod in the radial shaft 143c and the axial shaft 145c of each connecting piece 142c may be movably accommodated between the two clamping units 122c of each corresponding stop block.

Figure 23:
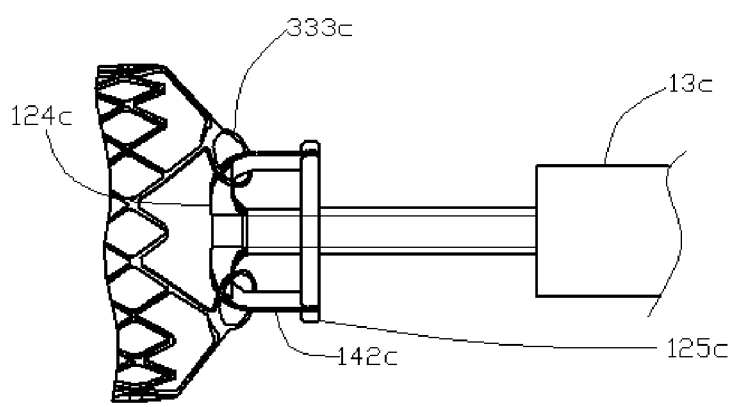
FIG. 23 is an exemplary schematic diagram showing that the free ends of the axial shafts in FIG. 21 are locked into the first stopper.
Figure 24:
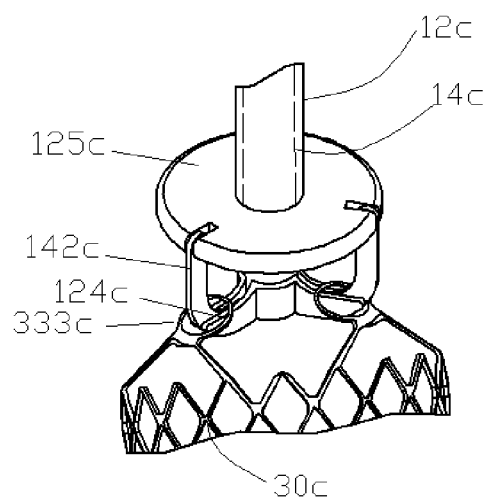
FIG. 24 is an exemplary schematic diagram from another angle of FIG. 23.

Putting the medical device 30c into the delivery device 10c includes the following steps: first, referring to FIG. 24, the multiple connecting rings 333c of the medical device 30c are hung onto the axial shafts 145c of the corresponding connecting pieces 142c one by one, and each connecting ring 333c is onto the corresponding stop block 124c; second, referring to FIG. 23, the sheath core 14c is actuated to move relative to the push rod 12c towards the proximal end, and the moving sheath core 14c actuates the connecting unit 121c to move towards the proximal end until the free ends of the axial shafts 145c enter the corresponding stop cavities 126c of the first stopper 125c, and each radial shaft 143c is accommodated between the two parallel clamping units 122c of the corresponding stop block 124c; and finally, as in the first embodiment, a loader (not shown in the figure) is arranged on the medical device 30c in a sleeving manner, the sheath 13c is actuated to move relative to the push rod 12c towards the distal end, and the loader is actuated to move along with the sheath 13c towards the distal end until the medical device 30c may be completely put into the sheath 13c in a compressed state.

After channels for interventional therapy are built in a human body, the distal end of the delivery device 10c with the medical device 30c is delivered to a lesion position. When the medical device 30c has arrived at an appointed lesion position, the sheath 13c is actuated to slowly move relative to the push rod 12c towards the proximal end. Referring to FIG. 23 and FIG. 24, the medical device 30c is gradually changed from the compressed state to an expanded state due to its self-expandability when the radial restriction from the sheath 13c to the medical device 30c disappears gradually and the connecting rings 333c of the medical device 30c outwards move along the radial directions of the radial shafts 143c in a process that the sheath 13c moves towards the proximal end. After the whole medical device 30c is completely extended out of the sheath 13c, an operator observes whether the medical device 30c achieves the therapeutic effect or not with equipment such as X-ray equipment or ultrasonic equipment. If the medical device 30c is located at a non-ideal position, the sheath 13c is actuated to move relative to the push rod 12c towards the distal end, and the medical device 30c is compressed into the sheath 13c again in this process. To adjust the position of the medical device 30c, the above processes can be repeated if necessary until the medical device 30c achieves an ideal therapeutic effect.

Figure 25:
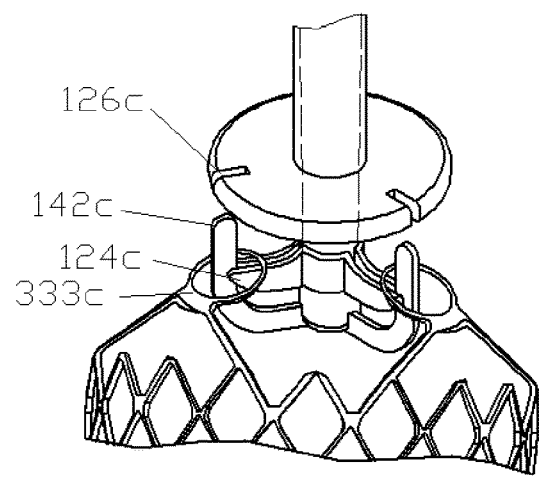
FIG. 25 is an exemplary schematic diagram showing that the free ends of the axial shafts are separated from the first stopper.
Figure 26:
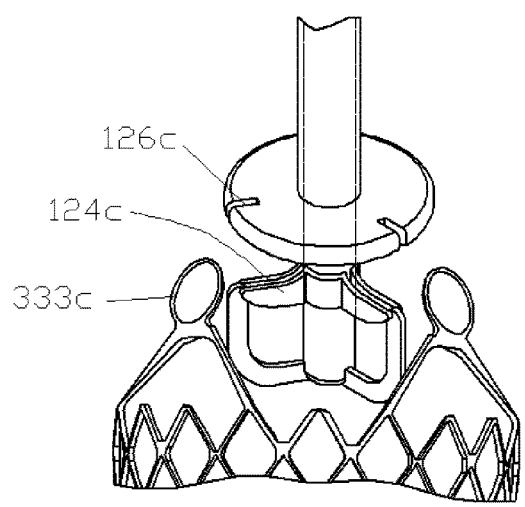
FIG. 26 is an exemplary schematic diagram showing that the medical device is completely separated from the delivery device.

Referring to FIG. 25 and FIG. 26, after the medical device 30c achieves an expected effect on the lesion, the sheath 13c is actuated again to move relative to the push rod 12c towards the proximal end until the whole lock member 15c is completely exposed. Then, the sheath core 14c is actuated to move relative to the push rod 12c towards the distal end, and the moving sheath core 14c actuates the connecting pieces 142c of the lock member 15c to move relative to the stop blocks 124c towards the distal end, that is, the connecting rings 333c move relative to the connecting pieces 142c towards the proximal end under the pushing of the stop blocks 124c until the connecting rings 333c are completely separated from the connecting pieces 142c. At the moment, the medical device 30c is completely separated from the lock member 15c of the delivery device 10c, thereby completing releasing the medical device 30c.

It can be known from the above structural description, loading process and implantation process, by cooperative use of the stop unit 121c and the connecting unit 141c, on one hand, the circumferential movement of the two clamping units 122*c* of each stop block 124*c* is restrained by each corresponding connecting piece 142*c*, which prevents a great distortion of each connecting ring of the medical device connected with each stop block 124*c* in the circumferential direction and reduces the possibility of movement of the medical device in the circumferential direction, and on the other hand, because of the fact that each radial shaft 143*c* may be accommodated between the two clamping units 122*c* of each corresponding stop block 124*c*, each connecting ring, connected with each stop block 124*c*, of the medical device may move on each corresponding radial shaft 143*c*, which buffers the outward expansion force of the medical device and lowering the injury to the human body. In addition, the circumferential thickness of each axial shaft 145*c* is slightly less than the distance between the two clamping units 122*c* of each corresponding stop block 124*c*, so that the free end of each axial shaft 145*c* at least may be partially covered by the two clamping units 122*c* of each corresponding stop block 124*c*, thereby preventing each connecting ring of the released medical device from being hooked by the free end of each axial shaft 145*c* again and improving the releasing efficiency of the medical device. Moreover, when the lock member 15*c* in the present embodiment is used to connect the connecting rings of the medical device, the connecting rings of the medical device may be hung onto one radial shaft 143*c*, that is, the connecting rings of the medical device may be closer to the center axis of the sheath core 14*c*, so that the medical device accommodated by the delivery device 10*c* in the present embodiment has a relatively small compressed outer diameter.

In other embodiments, the groove bottom of each stop cavity 126*c* may further continuously extend towards the push rod 12*c* along the radial direction, that is, the radial length of each stop cavity 126*c* may be equal to or slightly less than the radius of the first stopper 125*c*. In other embodiments, two adjacent clamping units 122*c* in two adjacent stop blocks 124*c* may be connected to be integrally formed so as to form a structure similar to the first stopper 125*c* as long as a space capable of accommodating each corresponding connecting piece 142*c* is reserved between the two clamping units 122*c* of each stop block 124*c*. Therefore, the multiple stop blocks 124*c* may form a push-out disc provided with multiple grooves in a circumferential surface. Each groove is the gap between two clamping units 122*c*.

In other embodiments, the distal end of the sheath core also may be connected with a hollow anti-injury head which is gradually thinned from the proximal end to the distal end to prevent the distal end of the sheath core from injuring human tissues in the delivery process.

Figure 27:
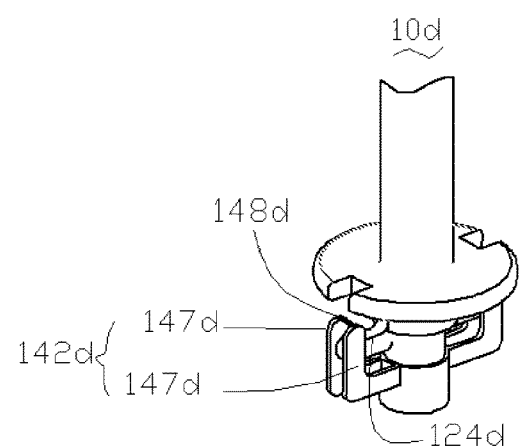
FIG. 27 is an exemplary schematic diagram of a delivery device provided by a fourth embodiment.

Referring to FIG. 27, a delivery device 10*d* provided by a fifth embodiment of the present application is basically the same as the delivery device 10*b* in the third embodiment. A difference lies in that a blocking strip 148*d* is at the proximal ends of two connecting subpieces 147*d* of each connecting piece 142*d* of the delivery device 10*d* of the present embodiment, and is used for preventing each stop block 124*d* from being separated from each corresponding connecting piece 142*d* in a process of releasing the medical device, thereby reducing the risk that each stop block 124*d* is staggered from each corresponding connecting piece 142*d* and improving the efficiency for installing the medical device onto the delivery device 10*d*. It can be understood that due to the existence of the blocking strips 148*d*, no first blocking member and no second blocking member are required to be arranged on the push rod and the sheath core of the delivery device of the present embodiment.

It can be understood that if each axial shaft 145 in the first embodiment is perforated to form an axial through-hole which penetrates through the inner side surface and the outer side surface of the axial shaft 145 but does not penetrate through the end face of the free end of the axial shaft 145, and the free end of each stop block 124 may slide axially in the through-hole, no first blocking member and no second blocking member are required to be arranged on the push rod and the sheath core of the delivery device. Of course, it can be understood that if multiple blockers are required or desired, the first blocking member and the second blocking member may be also respectively arranged on the push rod and the sheath core in the present embodiment according to an actual requirement.

Figure 28:
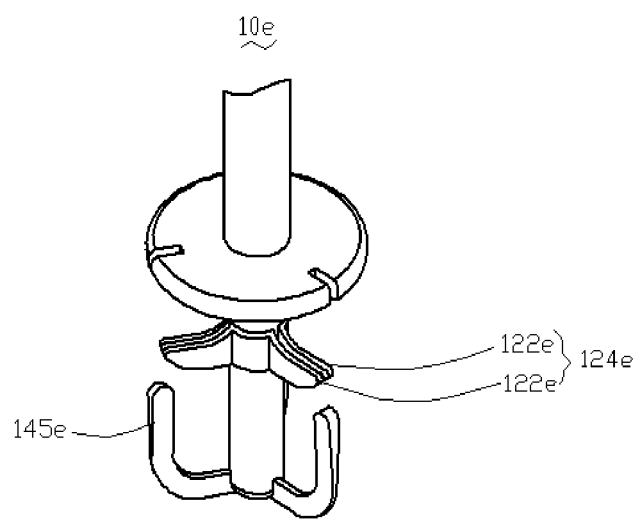
FIG. 28 is an exemplary schematic diagram of a delivery device provided by a fifth embodiment.

Referring to FIG. 28, a delivery device 10*e* provided by a sixth embodiment of the present application is basically the same as the delivery device 10*c* in the fourth embodiment. A difference lies in that the circumferential thickness of the proximal end of each axial shaft 145*e* of the delivery device 10*e* of the present embodiment is greater than that of the rest part of the same axial shaft 145*e*. Furthermore, the circumferential thickness of the proximal end of each axial shaft 145*e* is greater than the circumferential distance between two clamping units 122*e* of the stop block 124*e* corresponding to the same axial shaft 145*e*, and the circumferential thickness of the rest part of the same axial shaft 145*e* is less than the circumferential distance between two clamping units 122*e* of the stop block 124*e* corresponding to the same axial shaft 145*e*. In this way, each stop block 124*e* may be prevented from being separated from each corresponding axial shaft 145*e* in the process of releasing the medical device, thereby reducing the risk that each stop block 124*e* is staggered from each corresponding axial shaft 145*e* and improving the efficiency for installing the medical device onto the delivery device 10*e*. It can be understood that because of the fact that the circumferential length of the proximal end of each axial shaft 145*e* is greater than that of the rest part of the same axial shaft 145*e* and is also greater than the circumferential distance between the two clamping units 122*e* of the stop block 124*e* corresponding to the same axial shaft 145*e*, no first blocking member and no second blocking member are required to be respectively arranged on the push rod and the sheath core of the delivery device of the present embodiment. Of course, it can be understood that if multiple blockers are required, the first blocking member and the second blocking member may be also respectively arranged on the push rod and the sheath core in the present embodiment according to an actual requirement.

All technical features of the above embodiments may be randomly combined. To simplify the description, not all possible combinations of all the technical features in the above-mentioned embodiments are described. However, as long as the combinations of these technical features have no contradictions, they shall all fall within the scope of the description.

The above embodiments only express several implementation modes of the present application, and their descriptions are relatively specific and detailed, but may not be understood as limitations to the patent scope of the present application. It should be noted that persons ordinarily skilled in the art can further make a plurality of deformations and improvements without departing from the concept of the present application, and these deformations and improvements shall all fall within the protection scope of the present application. Therefore, the protection scope of the patent of the present application shall be based on attached claims.

The invention claimed is:

1. A delivery device for delivering a stent graft, comprising:
   a first stopper and a connecting unit, wherein the connecting unit is disposed opposite to the first stopper and is moveable relative to the first stopper;
   the connecting unit comprises a radial connecting portion and at least two axial shafts which are connected with the radial connecting portion and face the first stopper; and
   the connecting unit cooperated with the first stopper to form a closed lock space; and
   wherein the delivery device further comprises a second stopper disposed opposite to the first stopper; and when the connecting unit cooperates with the first stopper to form the lock space, the second stopper is located in the lock space;
   wherein the second stopper and the first stopper form a stop unit of the delivery device;
   the delivery device further comprises a push rod and a sheath core which is arranged on the push rod in a penetrating manner and is movable relative to the push rod in an arrangement selected from the group consisting of:
      the connecting unit arranged on the push rod, the stop unit arranged on the sheath core, and the connecting unit being closer to the proximal end of the delivery device than the stop unit; and
      the connecting unit arranged on the sheath core, the stop unit arranged on the push rod, and the stop unit being closer to a proximal end of the delivery device than the connecting unit; and
   wherein a first blocking member is arranged on the push rod, a second blocking member matched with the first blocking member is arranged on the sheath core, and the first blocking member is closer to a distal end of the delivery device than the second blocking member, and when the first blocking member is in contact with the second blocking member, the push rod is status relative to the sheath core.

2. The delivery device according to claim 1, wherein the second stopper comprises multiple stop blocks; and
   one stop block of the multiple stop blocks corresponds to at least one axial shaft of the at least two axial shafts.

3. The delivery device according to claim 2, wherein the multiple stop blocks are separated from one another.

4. The delivery device according to claim 3, wherein one stop block of the multiple stop blocks corresponds to one axial shaft of the at least two axial shafts;
   each stop block of the multiple stop blocks comprises two opposite and parallel clamping units; and
   a circumferential thickness of the axial shaft corresponding to the stop block is less than a circumferential distance between the two clamping units of the stop block corresponding to the same axial shaft.

5. The delivery device according to claim 2, wherein an end, which is close to the center axis of the sheath core, of each stop block is adjoined with an end, which is close to the center axis of the sheath core, of an adjacent stop block, and opposing ends, which are distant from the center axis of the sheath core, of each stop block are separated from one another.

6. The delivery device according to claim 2, wherein one stop block of the multiple stop blocks corresponds to two axial shaft of the at least two axial shafts;
   the connecting units comprises at least two connecting pieces, each of the two connecting pieces comprises two opposite and parallel connecting subpieces;
   each connecting subpiece comprising one axial shaft of the at least two axial shafts;
   each axial shaft comprises a radially inner surface and a radially outer surface, and each stop block comprises a radially outer end, the radially outer end of each stop block positioned a radial distance from the center axis of the sheath core that corresponds to a distance between the distance measured from the center axis to the radially inner surface and the distance measured from the center axis to the radially outer surface of the two axial shafts corresponding to the same stop block; and
   a circumferential thickness of each stop block is less than a circumferential distance between the two axial shafts corresponding to the same stop block.

7. The delivery device according to claim 1, wherein when the delivery device comprises the arrangement wherein the connecting unit is arranged on the sheath core and the stop unit is arranged on the push rod,
   the second stopper comprises multiple stop blocks, each of the multiple stop blocks corresponding to one axial shaft of the at least two axial shafts;
   each of the multiple stop blocks comprises two opposite and parallel clamping units;
   a circumferential thickness of the proximal end of each axial shaft is greater than that the circumferential thickness of a remainder of the same axial shaft;
   the circumferential thickness of the proximal end of the same axial shaft is greater than a circumferential distance between the clamping units of the stop block corresponding to the same axial shaft; and
   the circumferential thickness of the remainder of the same axial shaft is less than the circumferential distance between the two clamping units of the stop block corresponding to the same axial shaft.

8. The delivery device according to claim 1, wherein the connecting unit comprises at least two connecting pieces, each of the at least two connecting pieces comprises two opposite connecting subpieces;
   each connecting subpiece comprises one axial shaft of the at least two axial shafts; and
   a blocking strip is erected between the two axial shafts of each connecting piece.

9. The delivery device according to claim 1, wherein the second stopper comprises multiple stop blocks, each of the multiple stop blocks corresponds to one axial shaft of the at least two axial shafts;
   an axial through-hole is formed in the one axial shaft, the axial through-hole penetrates through an inner side surface and an outer side surface of the one axial shaft and does not penetrate through an end face of a free end of the one axial shaft; and
   a free end of one stop block is movably accommodated in the axial through-hole.

10. The delivery device according to claim 1, wherein the connecting unit comprises at least two connecting pieces, each of the connecting pieces comprises two opposite connecting subpieces;
   each connecting subpiece comprises one axial shaft of the at least two axial shafts; and
   a blocking strip is between the two axial shafts of each connecting piece.

11. The delivery device according to claim 1, wherein the second stopper comprises multiple stop blocks, each of the multiple stop blocks corresponds to one axial shaft of the at least two axial shafts;
- an axial through-hole is formed in the one axial shaft which penetrates through an inner side surface and an outer side surface of the one axial shaft and does not penetrate through an end face of a free end of the one axial shaft; and
- a free end of one stop block of the multiple stop blocks is movably accommodated in the axial through-hole.

12. The delivery device according to claim 1, wherein the radial connecting portion comprises at least two radial shafts; and
- one end of each axial shaft is connected with one radial shaft to substantially form an L shape.

13. The delivery device according to claim 1, wherein at least one connecting ring is arranged on the radial connecting portion.

14. The delivery device according to claim 1, wherein the first stopper comprises at least two stop cavities, and at least one of the at least two stop cavities is capable of accommodating a free end of at least one axial shaft of the at least two axial shafts.

15. The delivery device according to claim 14, wherein each of the at least two stop cavities is selected from a group consisting of a through-hole penetrating through a proximal-end surface and a distal-end surface of the first stopper or a groove which is sunken from part of a side surface of the first stopper toward the center of the first stopper and penetrated through the proximal-end surface and the distal-end surface of the first stopper.

16. The delivery device according to claim 1, wherein an inner side surface of the radial connecting portion is connected with inner side surfaces of the at least two axial shafts to form a hemispherical surface.

17. The delivery device according to claim 16, wherein an outer side surface of the radial connecting portion is connected with outer side surfaces of the at least two axial shafts to form a hemispherical surface.

* * * * *